United States Patent
Dupont et al.

(10) Patent No.: US 7,074,957 B2
(45) Date of Patent: Jul. 11, 2006

(54) PROCESS FOR PREPARING (METH)ACRYLIC ANHYDRIDE

(75) Inventors: Bernard Dupont, Creutzwald (FR); Jean-Michel Paul, Metz (FR)

(73) Assignee: Arkema, Cedex Paris la Defense (FR)

( * ) Notice: Subject to any disclaimer, the term of this patent is extended or adjusted under 35 U.S.C. 154(b) by 843 days.

(21) Appl. No.: 10/186,017

(22) Filed: Jun. 28, 2002

(65) Prior Publication Data

US 2003/0018217 A1 Jan. 23, 2003

(30) Foreign Application Priority Data

Jul. 6, 2001 (FR) .................................. 01 09009

(51) Int. Cl.
*C07C 65/00* (2006.01)
(52) U.S. Cl. ..................................................... 562/888
(58) Field of Classification Search ................. 562/893
See application file for complete search history.

(56) References Cited

U.S. PATENT DOCUMENTS 4,857,239 A * 8/1989 Hurtel et al. ............... 562/896
2002/0161260 A1 10/2002 Schmitt et al.

* cited by examiner

*Primary Examiner*—Paul A. Zucker
(74) *Attorney, Agent, or Firm*—Millen, White, Zelano, Branigan, P.C.

(57) ABSTRACT

A process for the batchwise preparation of (meth)acrylic anhydride, in which acetic anhydride is reacted with (meth) acrylic acid and the acetic acid is at least partly removed gradually as it is formed. In the process, the acetic acid removed is at least partly replaced by introducing into the reaction medium, during the reaction, acetic anhydride and/or (meth)acrylic acid. The (meth)acrylic anhydride obtained by this process may be used in the synthesis of (meth)acrylic thioesters, (meth)acrylic amides and (meth)acrylic esters, in polymerization reactions or as crosslinking agents.

26 Claims, No Drawings

PROCESS FOR PREPARING (METH)ACRYLIC ANHYDRIDE

CROSS REFERENCE TO RELATED APPLICATION

This application claims priority to French Patent Application No. 01 09 009 filed Jul. 6, 2001.

The present invention relates to a process for the batchwise preparation of (meth)acrylic anhydride.

Acrylic and methacrylic anhydrides are reagents of choice in the the synthesis of (meth)acrylic thioesters, (meth)acrylic amides and (meth)acrylic esters, in particular of tertiary alcohols that cannot be obtained by standard esterification/transesterification processes.

They are also used in polymerization reactions or as crosslinking agents.

It has been known for a long time that it is possible to prepare an anhydride by reacting acetic anhydride with the acid corresponding to the desired anhydride.

As early as 1934, French patent No. 784 458 described the preparation of propanoic, butyric and caproic anhydride by reacting acetic anhydride with propanoic acid, butyric acid and caproic acid, respectively.

In 1979, European patent application No. 4 641 provided the public with a continuous or batchwise process for preparing carboxylic acid anhydrides such as benzoic, hexahydrobenzoic and trimethylacetic anhydride, by reacting, in reaction/distillation apparatus, the corresponding acids with acetic anhydride, preferably in stoichiometric proportions.

In 1986, German patent application No. 3 510 035 disclosed a process for continuously preparing carboxylic acid anhydrides such as acrylic or methacrylic anhydride by reacting, in a distillation column and in the presence of a catalyst such as sulphuric acid or sulphonic or phosphoric acids, acetic anhydride with the acid corresponding to the desired anhydride.

In 1987, French patent application No. 2 592 040 proposed a process for the batchwise synthesis of (meth)acrylic anhydride by reacting acetic anhydride with (meth)acrylic acid in the presence of polymerization inhibitors. According to this process, acetic anhydride and (meth)acrylic acid are first reacted together, the acetic acid formed during the reaction is withdrawn and a distillation is then carried out. The molar ratio between the (meth)acrylic acid and the acetic acid is chosen between 0.5 and 5 and preferably between 2 and 2.2.

However, the implementation of this process comes up against polymerization problems. In addition, the amount of anhydride produced is limited by the size of the reactor and thus by the amount of reagents loaded into this reactor.

The aim of the present invention is thus to propose a process for preparing (meth)acrylic anhydride which offers higher production efficiency and a reduction or even elimination of the risks of polymerization.

One subject of the invention is thus a process for the batchwise preparation of (meth)acrylic anhydride, in which acetic anhydride is reacted with (meth)acrylic acid and at least some of the acetic acid is removed gradually as it is formed.

This process is characterized in that the acetic acid removed is at least partly replaced by introducing into the reaction medium, during the reaction, acetic anhydride and/or (meth)acrylic acid.

Such a process allows a greater than 35% increase in production efficiency compared with the prior art processes.

Other characteristics and advantages of the invention will now be described in detail in the description that follows.

DETAILED DESCRIPTION OF THE INVENTION

The invention is based on the surprising discovery made by the Applicant, namely that, by means of an astute distribution of the reagents, it is possible to obtain large gains in production per batch (batchwise) of (meth)acrylic anhydride, without increasing the reaction time.

This very large increase in production per batch is obtained with an identical initial mass of reagents (acetic anhydride and (meth)acrylic acid).

This initial charge is preferably the maximum charge permitted by the volume of the reactor.

Thus, according to the invention, the acetic acid, which is formed by reaction of the acetic anhydride and which is at least partly removed gradually as it is formed, is replaced with one and/or the other of the reagents.

In other words, an amount of the reagent(s) is added to occupy the space liberated by the removal of the acetic acid.

Preferably, all the acetic acid that is formed during the reaction is removed, gradually and as it is formed, by distillation.

In order to optimize the production of (meth)acrylic anhydride, it is desirable to replace, by means of the reagent(s), all the acetic acid removed.

In addition, a continuous addition of the reagent(s) throughout the reaction time is a variant that is preferable to an irregular addition.

It is also preferable that this addition should follow, as closely as possible, the removal of the acetic acid.

This is then reflected by a virtually total occupation of the volume of the reactor throughout the reaction.

Preferably, only one of the reagents is added.

The reagent added is advantageously acetic anhydride.

Furthermore, the initial charge introduced into the reactor preferably has an initial molar ratio $R_0$ of the (meth)acrylic acid to the acetic anhydride of between 2.5 and 11 and in particular between 9 and 11.

The overall molar ratio $R_g$ of the (meth)acrylic acid to the acetic anhydride is preferably between 0.5 and 5 and in particular between 1.8 and 2.2.

The reaction may be carried out in a reactor on which is mounted a distillation column.

In general, the reactor is stirred and heated by circulating heat-exchange fluid in a jacket or by recirculation through an external heat exchanger.

The distillation column preferably has a separating efficiency of greater than 10 theoretical plates and in particular greater than 12 theoretical plates. This makes it possible to minimize the losses of acetic anhydride via the first distillation fraction, which in this case consists to more than 99% of acetic acid, to work at low levels of reflux (R/C less than or equal to 2/1) and consequently to reduce the reaction time and the risks of polymerization that increase as the reaction time increases.

The column packing may be a standard packing, in bulk form or structured, or a mixture of these two types of packing.

The reaction temperature is generally between 50 and 120° C. and preferentially between 85 and 105° C.

The pressure is adjusted as a function of the chosen reaction temperature. In general, it is between 20 and 200 mm Hg (0.0267 and 0.2666 bar).

The reaction may be carried out in "isobar" mode, i.e. by fixing the pressure and allowing the temperature to change up to a limit value preferably fixed between 90 and 150° C., or in "isothermal" mode, i.e. by fixing the temperature and adjusting the pressure in the plant throughout the reaction so as to maintain this pressure.

The temperature at the column head is advantageously adjusted during the reaction, as a function of the pressure, so as to correspond to the distillation temperature of acetic acid.

By working in this way, a head fraction containing more than 99% acetic acid is obtained.

According to one preferred embodiment of the invention, the reaction between acetic anhydride and (meth)acrylic acid is carried out in the presence of at least one polymerization inhibitor.

In addition, a double-stabilization is preferably carried out, by introducing at least one inhibitor into the reactor and at least one inhibitor into the distillation column.

The inhibitors must be active with respect to polymerization while at the same time being inert with regard to the anhydrides and the (meth)acrylic acid.

Thus, all risk of polymerization in the reactor and the column is avoided.

The inhibitor for the reactor is advantageously chosen from the group consisting of 2,4-dimethyl-6-tert-butylphenol ("Topanol A") and 2,6-di-tert-butyl-para-cresol ("BHT"), and mixtures thereof.

The inhibitor for the distillation column is advantageously chosen from the group consisting of hydroquinone ("HQ"), 2,4-dimethyl-6-tert-butylphenol, 2,6-di-tert-butyl-para-cresol and phenothiazine, and mixtures thereof.

As regards the amounts to be used, the reactor inhibitor is preferably introduced into the initial charge of reagents in a proportion of at least 0.001% (1000 ppm) by weight of the charge.

The distillation column inhibitor is preferably introduced into the distillation column throughout the reaction, for example as a 5% solution (by weight relative to the total weight of the solution) in acetic acid. The flowrate of introduction of the column inhibitor is adjusted so as to have less than 1000 ppm of inhibitor in the final reactor product.

Sparging with depleted air (8% oxygen and 92% nitrogen by volume) may be carried out throughout the reaction.

The crude product obtained is generally perfectly clear, free of polymers and able to be freed of the head fraction by distillation under reduced pressure (for example of 20 mm Hg) so as to rid it of the excess acetic acid, of (meth)acrylic acid and of the compound formed by reaction of 1 mole of (meth)acrylic acid with 1 mole of acetic anhydride.

The process according to the invention may comprise a further step of distillation of the crude product obtained, where appropriate after removal of the head fraction, on a distillation column or using a short-residence-time machine such as a film evaporator.

EXAMPLES

The examples that follow illustrate the present invention without, however, limiting its scope. The percentages therein are expressed on a mass basis.

The following abbreviations are used therein:
MAA: methacrylic acid
AA: acrylic acid
MA$_2$OA: methacrylic anhydride
A$_2$OA: acrylic anhydride
Ac$_2$O: acetic anhydride
AcOH: acetic acid
Mixed: H$_2$C=CHCOOOCCH$_3$, or, depending on the case,

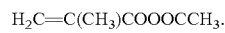

H$_2$C=C(CH$_3$)COOOCCH$_3$.

Example 1 (Comparative)

361 g (3.54 mol) of Ac$_2$O and 639 g (7.43 mol) of MAA (the molar ratio R$_0$ is thus 2.1) are introduced into a mechanically stirred reactor heated by circulation of thermostatically-maintained oil in a jacket, and on which is mounted a distillation column containing Multiknit® structured packing having a separation efficacy of 12 theoretical plates, and being able to function under vacuum.

1.09 g of Topanol A are introduced as inhibitor into the reactor, and a solution of 5% Topanol A and 5% HQ in acetic acid is introduced as inhibitor into the column, this solution being added uniformly throughout the duration of the reaction at a rate of 2 ml/h.

Sparging with depleted air (8% oxygen and 92% nitrogen by volume) is maintained in the reactor throughout the operation.

The acetic acid formed is removed gradually as it is formed. The first fraction distilled off is composed of 99.5% acetic acid.

After reaction for 6 hours 30 minutes at 95° C., the crude reaction product has the following composition:

| | |
|---|---|
| AcOH | 0.5% |
| Ac$_2$O | 0.06% |
| MAA | 11.8% |
| Mixed | 4.6% |
| MA$_2$OA | 81.6% |
| Side products | 1.44% |
| TOTAL | 100% |

The amount of MA$_2$OA contained in the crude product (measured by weighing at the end of the reaction) is 485 g.

Thus, the degree of conversion of Ac$_2$O into MA$_2$OA and Mixed is 96.5%.

The final molar ratio R$_f$ MAA/Ac$_2$O is 2.1; it is identical to the initial molar ratio.

The crude product obtained is then freed of the head fraction under reduced pressure (20 mm Hg) in order to remove therefrom the residual MAA and the Mixed.

The crude product obtained after removal of the head fraction consists of 96.2% MA$_2$OA.

Example 2 (According to the Invention)

The process is performed as indicated in Example 1, except that the same mass (1000 g) of overall initial charge of MAA and of Ac$_2$O is added to the reactor, but with more MAA and less Ac$_2$O being introduced.

The initial charge thus consists of 900 g (10.465 mol) of MAA and 100 g (0.98 mol) of Ac$_2$O (the initial molar ratio R$_0$ is 10.7).

The same inhibitor as in Example 1 is introduced in the same proportion into the reactor.

The same inhibitor solution as in Example 1 is introduced at the same flowrate into the column.

Ac$_2$O is introduced uniformly throughout the reaction, gradually as the AcOH is removed, so as to occupy all the space liberated by the said AcOH in the reactor.

Working in this way allows optimum occupation of the reaction volume.

After reaction for 6 hours 30 minutes at 95° C., the amount of $Ac_2O$ introduced continuously during the reaction was 408 g and the crude reaction product has the following composition:

| | |
|---|---|
| AcOH | 0.4% |
| $Ac_2O$ | 0.2% |
| MAA | 12.3% |
| Mixed | 7.2% |
| $MA_2OA$ | 78.8% |
| Side products | 1.44% |
| TOTAL | 100% |

The amount of $MA_2OA$ contained in the crude product (measured by weighing at the end of reaction) is 680 g, for a total amount of reagent used of 1408 g (1000+408).

The final molar ratio $R_f$ is 2.1, as in Example 1.

Consequently, the gain in production of $MA_2OA$ is 40% relative to Example 1, without increasing the reaction time and with the same final molar ratio $R_f$.

Thus, for the same reaction volume (same initial mass of 1000 g), but with a better distribution of the reagents, much more $MA_2OA$ was produced.

The degree of conversion of $Ac_2O$ into $MA_2OA$ and Mixed is 97%.

The crude product obtained after removal of the head fraction is entirely clear, free of polymers and able to be distilled under reduced pressure (20 mm Hg). It consists of 96.4% $MA_2OA$.

Example 3 (Comparative) and Example 4 (According to the Invention)

The process as indicated in Examples 1 and 2 is performed, replacing the methacrylic acid with acrylic acid and using a distillation column having an efficacy of 20 theoretical plates.

All the other conditions are identical to those of Examples 1 and 2.

At the end of the 6 hours 30 minutes of reaction at 95° C., the following table may be produced:

| Synthesis $A_2OA$ | Example 3 (comparative) | Example 4 (according to the invention) |
|---|---|---|
| AA charged at the start (g) | 535 | 735 |
| $Ac_2O$ charged at the start (g) | 361 | 161 |
| Total charged at the start (g) | 896 | 896 |
| $Ac_2O$ introduced continuously during the reaction | 0 | 335 |
| Total charged (g) throughout the operation | 896 | 1231 |
| $A_2OA$ produced (g) | 360 | 497 |

The gain in production for Example 4 relative to Example 3 is thus 38%.

The invention claimed is:

1. Process for the batchwise preparation of (meth)acrylic anhydride, in which acetic anhydride is reacted with (meth)acrylic acid and at least some of the acetic acid is removed gradually as it is formed, wherein the acetic acid removed is at least partly replaced by introducing into the reaction medium, during the reaction, a reagent comprising acetic anhydride and/or (meth)acrylic acid.

2. Process according to claim 1, in which the reagent introduced is acetic anhydride.

3. Process according to claim 2, in which the initial molar ratio R0 of the (meth)acrylic acid to the acetic anhydride is between 2.5 and 11.

4. Process according to claim 2, in which the overall molar ratio of the (meth)acrylic acid to the acetic anhydride is between 0.5 and 5.

5. Process according to claim 3, in which the overall molar ratio of the (meth)acrylic acid to the acetic anhydride is between 0.5 and 5.

6. Process according to claim 1, in which all the acetic acid which is formed during the reaction is removed gradually as it is formed.

7. Process according to claim 2, in which all the acetic acid which is formed during the reaction is removed gradually as it is formed.

8. Process according to claim 3, in which all the acetic acid which is formed during the reaction is removed gradually as it is formed.

9. Process according to claim 1, in which all the acetic acid removed is replaced with (meth)acrylic anhydride and/or (meth)acrylic acid.

10. Process according to claim 2, in which all the acetic acid removed is replaced with (meth)acrylic anhydride and/or (meth)acrylic acid.

11. Process according to claim 3, in which all the acetic acid removed is replaced with (meth)acrylic anhydride and/or (meth)acrylic acid.

12. Process according to claim 4, in which all the acetic acid removed is replaced with (meth)acrylic anhydride and/or (meth)acrylic acid.

13. Process according to claim 1, in which the introduction of acetic anhydride and/or of (meth)acrylic acid is performed continuously throughout the reaction.

14. Process according to claim 1, in which the reaction is carried out in a reactor on which is mounted a distillation column.

15. Process according to claim 14, in which the distillation column has a separation efficacy of greater than 10 theoretical plates.

16. Process according to claim 1, in which the reaction between the acetic anhydride and the (meth)acrylic acid is carried out in the presence of at least one polymerization inhibitor.

17. Process according to claim 1, in which the reaction is carried out in a reactor on which is mounted a distillation column and in which at least one polymerization inhibitor is introduced into the reactor and at least one polymerization inhibitor is introduced into the distillation column.

18. Process according to claim 17, in which:
   the polymerization inhibitor introduced into the reactor is chosen from the group consisting of 2,4-dimethyl-6-tert-butylphenol and 2,6-di-tert-butyl-para-cresol, and mixtures thereof; and the polymerization inhibitor introduced into the distillation column is chosen from the group consisting of hydroquinone, 2,4-dimethyl-6-tert-butylphenol, 2,6-di-tert-butyl-para-cresol and phenothiazine, and mixtures thereof.

19. Process according to claim 18, in which:

the polymerization inhibitor introduced into the reactor is introduced into the initial charge of reagents, in a proportion of at least 0.001% by weight; and the polymerization inhibitor introduced into the distillation column is introduced into the distillation column throughout the reaction.

20. Process according to claim 2, in which the initial molar ratio R0 of the (meth)acrylic acid to the acetic anhydride is between 9 and 11.

21. Process according to claim 2, in which the overall molar ratio of the (meth)acrylic acid to the acetic anhydride is between 1.8 and 2.2.

22. Process according to claim 3, in which the overall molar ratio of the (meth)acrylic acid to the acetic anhydride is between 1.8 and 2.2.

23. Process according to claim 14, in which the distillation column has a separation efficacy of greater than 12 theoretical plates.

24. Process according to claim 1, further comprising reacting the (meth)acrylic anhydride obtained to synthesize a (meth)acrylic thioester, (meth)acrylic amide or (meth)acrylic ester.

25. Process according to claim 1, further comprising polymerizing the (meth)acrylic anhydride obtained.

26. Process according to claim 1, further comprising conducting a reaction wherein the (meth)acrylic anhydride obtained is used as a crosslinking agent.

* * * * *